United States Patent
Hansen Fernández et al.

(10) Patent No.: US 9,550,702 B2
(45) Date of Patent: Jan. 24, 2017

(54) TUBULAR DIGESTER

(76) Inventors: Felipe Hansen Fernández, Santiago (CL); José Ignacio Labbé Silva, Santiago (CL); Patricio Andrés Salas Pérez, Santiago (CL)

( * ) Notice: Subject to any disclaimer, the term of this patent is extended or adjusted under 35 U.S.C. 154(b) by 77 days.

(21) Appl. No.: 14/375,697

(22) PCT Filed: Jul. 4, 2012

(86) PCT No.: PCT/CL2012/000030
§ 371 (c)(1),
(2), (4) Date: Jul. 30, 2014

(87) PCT Pub. No.: WO2014/005237
PCT Pub. Date: Jan. 9, 2014

(65) Prior Publication Data
US 2015/0000357 A1  Jan. 1, 2015

(51) Int. Cl.
*C12M 1/107* (2006.01)
*C05F 11/00* (2006.01)
(Continued)

(52) U.S. Cl.
CPC .............. *C05F 11/00* (2013.01); *C02F 3/2893* (2013.01); *C05F 17/027* (2013.01); *C12M 21/04* (2013.01);
(Continued)

(58) Field of Classification Search
CPC ....... C12M 21/04; C12M 23/06; C12M 23/14; C12M 23/26; C12M 23/36; C12M 29/06; C12M 29/08; C12M 29/24
See application file for complete search history.

(56) References Cited

U.S. PATENT DOCUMENTS 4,100,023 A * 7/1978 McDonald ................ C02F 3/28
435/167
4,514,297 A 4/1985 Enqvist
(Continued)

FOREIGN PATENT DOCUMENTS

EP 0563434 A1 10/1993
ES 8602551 A1 3/1986
(Continued)

OTHER PUBLICATIONS

Arnott, "The Biogas/Biofertilizer Business Handbook", PEACE CORPS publication (Jul. 1985), pp. 1-193.*
(Continued)

*Primary Examiner* — William H Beisner
(74) *Attorney, Agent, or Firm* — Ulmer & Berne LLP

(57) ABSTRACT

Contiguous flow anaerobic digester for mechanization of organic matter and production of fertilizer powering the conditions and performance of the anaerobic digestion process, through homogenization of the sludge and process temperature, wherein the digester is tubular shaped and comprises a biogas exhaust valve at the top of the digester. One end of the digester has a sludge outlet connection, a water- and gas-tight zipper that is resistant to the corrosive elements of digestion, and an outlet. The opposite end of the digester has a mud inlet, and a water- and gas-tight zipper that is resistant to the corrosive elements of digestion, wherein said digester further comprises at its base a gas irrigation system for biogas recirculation composed of a polymeric material resilient to the corrosive elements of anaerobic digestion.

9 Claims, 3 Drawing Sheets

(51) Int. Cl.
　　　C05F 17/02　　　(2006.01)
　　　C12M 1/00　　　(2006.01)
　　　C12P 5/02　　　(2006.01)
　　　C02F 3/28　　　(2006.01)
(52) U.S. Cl.
　　　CPC .............. *C12M 29/24* (2013.01); *C12P 5/023* (2013.01); *Y02E 50/343* (2013.01); *Y02P 20/145* (2015.11); *Y02W 30/43* (2015.05); *Y02W 30/47* (2015.05)

(56)　　　　References Cited

U.S. PATENT DOCUMENTS

| 5,185,079 | A | 2/1993 | Dague | |
| 6,296,766 | B1* | 10/2001 | Breckenridge | C02F 3/006 210/603 |
| 2002/0079266 | A1 | 6/2002 | Ainsworth et al. | |
| 2006/0231488 | A1 | 10/2006 | McCune-Sanders | |
| 2008/0307574 | A1* | 12/2008 | Villgren | A47K 11/02 4/449 |
| 2010/0255526 | A1* | 10/2010 | Braet | B01F 3/04262 435/29 |

FOREIGN PATENT DOCUMENTS

| WO | 2011021207 A2 | 2/2011 | | |
| WO | WO 2014004933 A1 * | 1/2014 | ............ | C12M 21/04 |

OTHER PUBLICATIONS

Lansing et al., "Quantifying electricity generation and waste transformations in a low-cost, plug-flow anaerobic digestion system", Ecological Engineering, vol. 34 (2008), pp. 332-348.*
Rodriquez, J. Moreno; International Search Report, issued in International Application No. PCT/CL2012/000030; mailed on Jan. 30, 2013; 5 pages, including English-language translation.
Serra, Renato; Written Opinion of the International Preliminary Examining Authority, issued in International Application No. PCT/CL2012/000030; mailed on May 13, 2014; 5 pages.
Levenspiel, Octave; Chemical Reaction Engineering; 1999; p. 90 of 684; 3rd Edition; John Wiley & Sons Inc., USA, (685 Pages Provided).
Henkel, Klaus-Dieter; Reactor Types and Their Industrial Applications; Ullmann's Encyclopedia of Industrial Chemistry; 2012; pp. 293-327; vol. 31; Wiley-VCH Berlag GmbH & Co. KGaA, Weinheim, Germany.
Denbigh, K.G. et al.; Chapter 3 Tubular Reactors; Chemical Reactor Theory: An Introduction; 3rd Edition; Cambridge University Press; 1 page.
Wikipedia; Plug flow reactor model; page last updated on Apr. 5, 2016; downloaded on Apr. 28, 2016 from https://en.wikipedia.org/wiki/Plug_flow_reactor_model; 4 pages.
Department of Chemical and Biological Engineering faculty at the University of Colorado Boulder, YouTube Video "Comparing CSTR and PFR Balances"; published on Feb. 12, 2013; viewable at https://www.youtube.com/watch?v=xrOdRKzlkcE&feature=youtu.be.

* cited by examiner

TUBULAR DIGESTER

The present invention relates to an anaerobic digester that is tubular shaped made from a series of polymers of high mechanical and chemical performance and resistant to UV, abrasion and other climatic conditions within which the anaerobic digestion of the organic material occurs (digestate) producing methane, where the biogas obtained is recirculated into the reactor via modular circuits, gas diffusers, and compounds of polymeric material resistant to corrosion produced by the anaerobic digestion. Such recirculation system of biogas, allows the hydrodynamic control of the reactor improving the operation and the process.

BACKGROUND OF THE INVENTION

At the industry and experimental level, different types of reactors designed to create optimal conditions for anaerobic digestion of organic waste are identified. At the industry level, according to the EPA (United States Environmental Protection Agency) in 2011 34% of the reactors were plug flow (PF) modified, 30% were full mix (MC), 13% were covered lagoons, the 13% were horizontal FP, and the remaining 10% was divided between reactors "Upflow Anaerobic Sludge Blanket" (UASB) to adehesa biomass and other gaps partially covered. In the past decade, the FP was the most common reactor. Only in recent years have MC digesters increased their presence in the U.S. market. On the other hand, in Europe the most common type of reactor is the MC. This is due to the fact that most of the biogas market in Europe is covered by the German companies that opt for this technology in building agricultural decentralized plants.

In a plug flow reactor, the most important function of the recirculation system of the digestate is to recycle the microorganisms grown during anaerobic digestion to inoculate fresh waste to the influent, i.e., increasing the concentration of the catalyst right where it is most needed. Another function of the recirculation is to increase the agitation of the reactor. By increasing the flow velocity increases turbulence in the reactor with it, the agitation. This implies that the agitation system by biogas and digestate recirculation can have the same purpose: to homogenize the content of the reactor. For example, in an EGSB ("expanded granular sludge bed") reactor a high flow recirculation, combined with the internal resistance due to the granular sludge is normally applied, it creates a good agitation. Another example is the agitation by pumped of the digestate in a reactor at MC. Note that to get a good stirring of the reactor by stirring, is necessary to move from laminar flow to turbulent flow by increasing the recirculation flow and/or hydraulic barriers.

Various anaerobic digesters are known from the prior art that aim to produce methane from the decomposition of organic material and then produce biogas. At the same time it is observed that there are various designs of reactors used for this purpose, as well as building materials used. It is also known front the prior art that for best results in the process of generation of gas from the anaerobic decomposition it is necessary to agitate the material residing within the reactor to maximize the action of the bacterial organisms and thus have better control of the pH, pressure and temperature of the biodigestion process.

ES 8602551 describes an anaerobic digestion tank for use in sewage wells with gas circulation pipes which open into the bottom of the tank, targeting the gas bubbling through the wells to shake thereto, where some these pipes are associated individually with heat exchange envelopes of heaters. Each gas circulation pipe opens to the lower part of the tank so that the gas exiting from the pipe does so in the direction towards the base of the tank and the bottom of the wells, so that the wells are drawn into below to collide on the tank base to remove sedimented materials and thus avoid the accumulation of these materials in the bottom of the tank.

For its part U.S. Pat. No. 5,185,079 describes an anaerobic process carried out in a pond where biological reaction occurs under anaerobic conditions and the pond is operated in a fill sequence. When waste enters into the reactor pond it is mixed with biogas or liquid recirculating and waste feed continues until the reactor is filled to its maximum predetermined level. Anaerobic reaction occurs with continuous or intermittent mixing and once it discontinues enables biomass to settle forming low solids. Alter sufficient time in the settling cycle, the liquid over low solids on the reactor is discarded decreasing the reactor contents to the predetermined low liquid level. The mixture of gas or liquid is recirculated again and she excess biomass from the reactor periodically wasted.

Document US 20060231488 describes a tubular digester system including a heat holding tank connected to a manifold which feeds one or multiple parallel injection pumps that force the filling through valves and into one or several parallel digesters hulls. The biogas produced by the digester is pressurized due to a liquid column effluent created by a high output. The filling material is put into contact with microorganisms that promote the generation of biogas which is stored by a collector whose release is controlled by a valve or regulator.

Finally, the document US 2002/0079266 discloses a system for converting the cellulose contained in the raw material into useful materials, which contains in one or more sludge feeders, two or more anaerobic pressurized digesters connected in parallel, each reactor containing a stirrer, a or more feed ports, one or more discharge ports, optional pressure regulator, and a reaction chamber, which supports the reaction solution containing anaerobic microorganisms that convert the aqueous slurry at least methane and enriched effluent. This invention is characterized by the use of high pressure for the process which range from more than 10 psi to 265 psi, in order to provide conditions for the decomposition of cellulose into useful materials.

Therefore, none of the prior art proposes the technical advantage of providing an anaerobic digestion reactor that facilitates the digestion of different types of organic matter on a continuous basis, in an economical, simple, accessible and adaptable to different agro-industrial processes way, being easily scalable through material and structural principles of geotechnical to lower costs and by control systems that made more flexible operability, optimizing their performance by means of hydrodynamic control reactor.

DESCRIPTION OF THE INVENTION

The objective of the present invention is to propose a tubular anaerobic digester for methanization of organic matter and production of substrate for fertilizers or agricultural applications by stirring biogas recirculation, generating a flow boosts the internal hydraulic, allowing a partial homogenization temperature and digestate processing that strength, giving stability, reducing maintenance costs, extending the range of total solids (TS) to be digested between 2% to 15% and allowing congestion.

The proposed solution is a tubular reactor made from a series of polymers with high mechanical properties, chemical which has incorporated a hermetically sealed inspection element that connects the interior with the exterior that allows the operation and maintenance of the system. It also has an instrumentation and automated control of the conditions within the reactor that allows control the process and adapt to different working conditions of anaerobic digestion.

The digester also has a biogas recycle system which allows control of internal hydrodynamic by modular reactor through modular diffusers arranged in circuits size and shape of the reactor to recirculate the gas produced by the methanization reincorporating it into the reactor.

The recirculation system is fixed to the base of the reactor in order to inject tire gas in form of bubbles rising from the bottom of the digester by the mud stirring it and potentiating the action of methanizer bacteria avoiding sedimentation of solids in the bottom of the reactor, allowing to administer such agitation according the convenience of the process.

Thanks to these characteristics, it provides an increase in the rate of mixture of microorganisms for a better execution of the process and a uniform temperature is obtained by reducing this mismatch problems pH mode.

Further, due to gas recirculation process generated, it is possible to obtain better dissolution of $CO_2$ thus increasing influent original alkalinity allowing the digestion of volatile solids range going from 15% to 20%, also allowing co-occurrence of different substrates.

Advantageously, thanks to the design of the reactor and due to the recirculation process explained above, it is possible to significantly reduce the residence time hydraulic (HRT). Thus it is clear to observe the advantages obtained from the invention proposed and which could not be obtained from the prior art since a design of tubular biodigester to solve the technical problem proposed in the manner proposed in this document is not observed.

The proposed invention will be better understood, and other objects, details, characteristics and advantages thereof will demonstrate more clearly with reference to the accompanying drawings below.

DETAILED DESCRIPTION OF THE INVENTION

Figure 1:
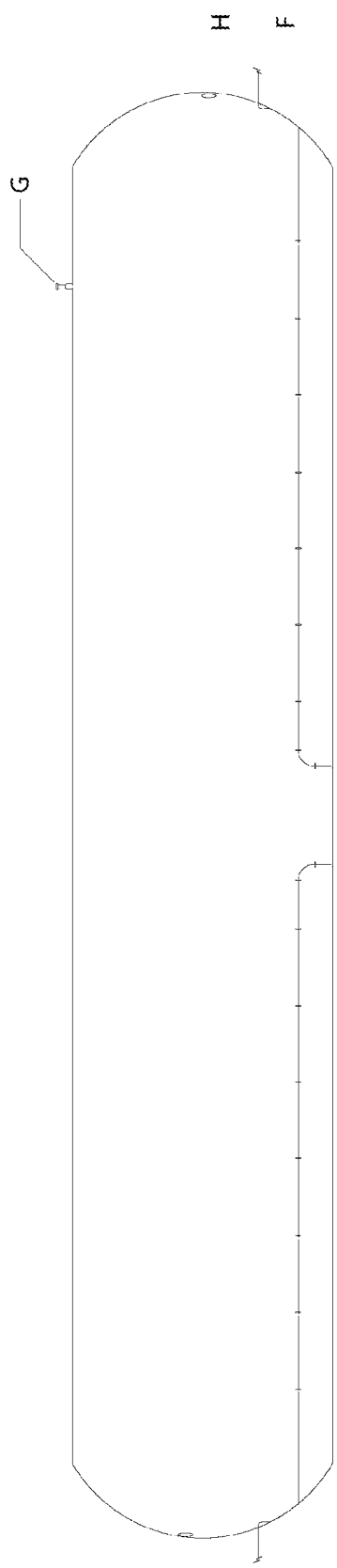
FIG. 1 shows a side view of a tubular anaerobic digester.

With reference to FIG. 1, the digester (A) from the present invention having at its top a biogas valve (G) arranged to control the output of the generated gas into the reactor for distribution is observed. Preferably the valve has been implemented according to the standard for natural gas network distribution.

The gas recirculation system from (H) is disposed in the bottom of the reactor. There is a drain (F) connected to the output of the digester (A) whose purpose is to evacuate fluids from the organic material towards the outside.

Figure 2:
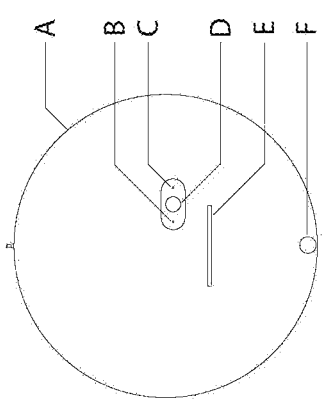
FIG. 2 shows a front view of the tabular anaerobic digester.

FIG. 2 shows a front view of the digester (A) which comprises a control system winch includes a thermometer (B) to measure the temperature at the outlet of the digester (A), it is also provided with a gauge (C) for measuring the pressure inside the reactor.

Under the mud inlet connection (D') is provided a hermetically sealed inspection element (E) which is sealed to water and gas, as well as resistant to corrosive elements of digestion, whose function is to connect the inside to the outside of the biodigester (A) to allow maintenance work.

Figure 3:
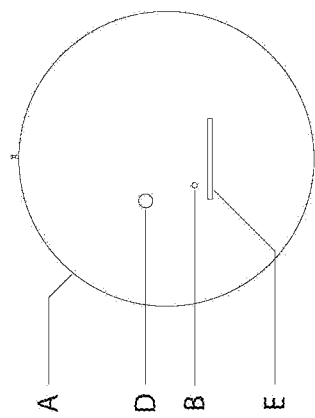
FIG. 3 shows a roar view of the tubular anaerobic digester.

As seen in FIG. 3 that has been placed in the bottom of the digester (A) a slurry inlet (D') used to be connected to the pipes carrying the organic material to be deposited in the digester (A) and a thermometer (B') to measure the temperature at the inlet of the digester. Furthermore it has been incorporated a hermetically sealed inspection element, which is sealed to water, gas and corrosive elements from the digestion (E').

Figure 4:
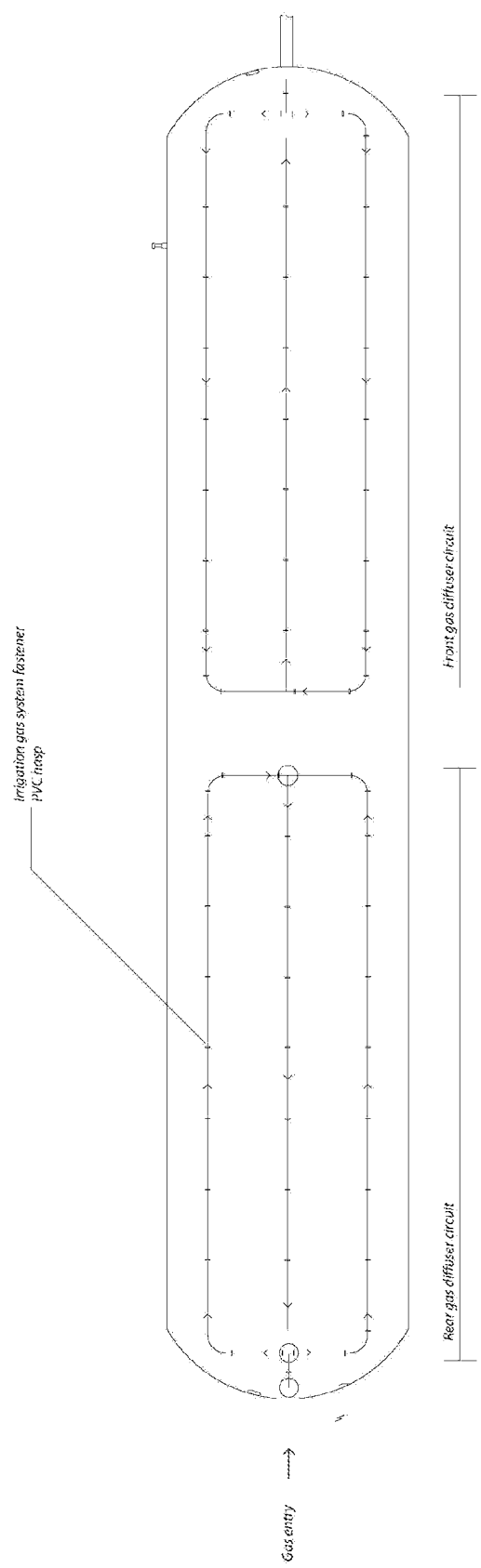
FIG. 4 shows a plan view of the tubular anaerobic digester where gas diffusers circuits are observed.

FIG. 4 shows the layout of the gas recirculation system in this case separated in two independent diffusers circuits that allow the gas to be recirculated through the interior of the digester (A).

The biodigester is a container made with a series of polymers with high chemical resistance to stress, UV, abrasion and other weather conditions which is made according to the availability of muds, ie, can vary in size depending on the amount of organic material to be treated within him or the gas demand required to be extracted.

The design also makes it possible that additionally to vary its size it can be arranged in series or parallel connected modules being adjustable to different scales treatments.

Experimentally, a tubular digester was designed as explained above 3.4 m in diameter, a length of 18.8 m and capacity of 170 $m^3$. Its materiality is composed of a number of polymeric materials, where each has its functional role.

The materials used allow chemical resistance to alkali, organic acids and volatile compounds as well as UV resistance, abrasion and water. As well as thermal insulation. The inlet and out of muds were made of PVC pipe of 16 cm.

Regarding the recirculation system were used microperforated polymeric hoses 24 m for front circuit and rear.

In the preferred embodiment, the organic material mixed with water is deposited into the digester (A) through a pipe connected to the inlet of sludge (D'). The temperature inside the digester (A) is measured by the thermometer (B). Once deposited organic material begins the process of digestion of organic matter due to the ideal conditions inside the digester achieved in tire present invention.

The gas generated by the digestion process is retained inside the reactor and part of it is recirculated by a gas blower (blower) by means of the front and rear gas recirculation system through micro apertures which have the hoses of the system, allowing tire to flow in the form of bubbles from the bottom of the digester passing through the organic matter and simultaneously generating a hydrodynamic movement.

Biogas valve (G) allows the gas to be removed from digester (A) to be consumed or used in a home network or the network type of convenience.

During the biodigestion process it can be required emptying the digester, for this purpose we have the drain path (F) to empty its contents towards the outside of the digester (A).

Meanwhile, the organic material that has been treated within the digester is removed for subsequent use as substrate for fertilizers or agricultural applications or recirculated to the digester (D'), thus proceeding to introduce a new quantity of organic material forming the natural inoculation for the process of biogas generation within the tubular anaerobic digester that is claimed below.

The invention claimed is:
1. A continuous flow anaerobic digester for methanization of organic matter and production of fertilizer powering the conditions and the performance of the anaerobic digestion process, by homogenization of the sludge and the process temperature characterized in that the digester (A) comprises a flexible polymer balloon of high chemical resistance to climatic conditions, of tubular shape, comprising an exhaust valve of biogas (G) located at a top of the digester (A), wherein an end of the digester (A) has a sludge outlet connection (D) and a zipper which is water-tight, gas-tight and resistant to corrosive elements of digestion (E) and is located in a middle portion of said end, and outlet (F) located in a lower part of said end, and wherein in an opposite end of the digester (A) there is a mud inlet (D') and a zipper which is water-tight, gas-tight and resistant to corrosive elements of digestion (E'), and is located in the middle portion of said opposite end, wherein said digester (A) further comprises at its base a gas irrigation system (H) for biogas recirculation comprising modular circuits diffusers composed of a polymeric material resistant to the corrosion of the elements of anaerobic digestion; wherein the gas irrigation system (H) is formed of hoses having micro-perforations such that gas coming from the gas irrigation system (H) is recirculated in the form of bubbles of biogas through the micro-perforations.

2. The anaerobic digester according to claim 1, wherein the middle portion of one end of the digester (A) further comprises a control system comprising automated instrumentation that comprises one or more of a thermometer, a manometer, valves, and probes.

3. The anaerobic digester according to claim 1, wherein the recirculated gas is generated by the digestion process within the digester (A).

4. The anaerobic digester according to claim 1, wherein the mud inlet (D'), the mud output connection (D), the drain (F) and the biogas valve (G) are constructed of material resistant to corrosion produced by the anaerobic digestion of compounds.

5. The anaerobic digester of claim 1, wherein the gas irrigation system (H) is separated into two independent circuits.

6. A method for obtaining biogas into a digester enhancing conditions and performance of an anaerobic digestion process by homogenization of mud and a process temperature, the method comprising the steps of:
providing a digester (A) comprising a flexible polymer balloon with high chemical resistance to stress, UV, abrasion and other climatic conditions, of tubular shape comprising a biogas valve (G) located in a top of the digester (A), wherein one end of the digester (A) has a mud outlet connection (D) and a zipper which is watertight (E) and gastight and resistant to corrosive elements of digestion and is located in a middle portion of said end, an outlet (F) located at a bottom of said end, an inlet of mud connection (D') at an opposite end of the digester (A) and a zipper which is watertight (E') and is located in the middle portion of said opposite end, wherein the digester (A) further comprises at its base a gas irrigation system (H) for recirculation of biogas comprising two gas diffusers circuits composed of micro perforated hoses;
depositing organic material mixed with water into the digester (A) through a pipe connected to the mud inlet (D') such that the process of digestion of organic matter inside the digester begins;
controlling various parameters inside the digester;
retaining the gas generated by the digestion process into a reactor and recirculating part of it through the gas irrigation system of biogas via the micro-perforations of the hoses of the irrigation system such that gas in the form of bubbles flows from the base of the digester passing through the organic matter and simultaneously agitating it.

7. The method for obtaining biogas according to claim 6, further comprising the step of allowing the gas to be removed from digester (A) through the biogas valve (G) to be consumed or used in a gas network.

8. The method for obtaining biogas according to claim 7, characterized in that the method further comprises the step of evacuating the contents of the digester outside of the digester (A) through a drain (F) in case the biodigestion process requires it.

9. The method for obtaining biogas according to claim 7, further comprising the step of removing organic material that has already been treated within the digester (A) through a connection pipe connected to the mud outlet (D') for its subsequent use as fertilizer.

* * * * *

UNITED STATES PATENT AND TRADEMARK OFFICE
CERTIFICATE OF CORRECTION

PATENT NO. : 9,550,702 B2
APPLICATION NO. : 14/375697
DATED : January 24, 2017
INVENTOR(S) : Felipe Hansen Fernandez et al.

It is certified that error appears in the above-identified patent and that said Letters Patent is hereby corrected as shown below:

On the Title Page
Item (57) in the Abstract section, Line 1, change "Contiguous" to --Continuous--;

In the Specification
Column 3, Line 12, change "tire" to --the--;
Column 3, Line 42, change "tabular" to --tubular--;
Column 3, Line 44, change "roar" to --rear--;
Column 3, Line 62, change "winch" to --which--; and
Column 4, Line 46, change "tire" to --the--.

Signed and Sealed this
Twenty-first Day of March, 2017

Michelle K. Lee
*Director of the United States Patent and Trademark Office*